(12) United States Patent
Yomota et al.

(10) Patent No.: US 11,678,833 B2
(45) Date of Patent: Jun. 20, 2023

(54) BRAIN ACTIVITY FEATURE AMOUNT EXTRACTION METHOD

(71) Applicant: Shimadzu Corporation, Kyoto (JP)

(72) Inventors: Satoshi Yomota, Kyoto (JP); Shin Nakamura, Kyoto (JP); Kenta Chinomi, Kyoto (JP); Nobuyuki Akinaga, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 560 days.

(21) Appl. No.: 16/781,174

(22) Filed: Feb. 4, 2020

(65) Prior Publication Data

US 2020/0268305 A1    Aug. 27, 2020

(30) Foreign Application Priority Data

Feb. 21, 2019    (JP) .............................. JP2019-029663

(51) Int. Cl.
     *A61B 5/00*      (2006.01)
     *A61B 5/026*      (2006.01)
     *A61B 5/16*      (2006.01)
     *G16H 40/63*      (2018.01)

(52) U.S. Cl.
CPC .......... *A61B 5/4064* (2013.01); *A61B 5/0261* (2013.01); *A61B 5/16* (2013.01); *A61B 5/6803* (2013.01); *A61B 5/7278* (2013.01); *A61B 5/7425* (2013.01); *G16H 40/63* (2018.01); *A61B 2503/12* (2013.01)

(58) Field of Classification Search
CPC .............................. A61B 2503/12; G16H 40/63
USPC ........................................................ 600/473
See application file for complete search history.

(56) References Cited

U.S. PATENT DOCUMENTS

| | | | |
|---|---|---|---|
| 2005/0209785 A1* | 9/2005 | Wells | G16B 40/30 702/19 |
| 2009/0155754 A1* | 6/2009 | Shankle | G09B 7/00 434/236 |
| 2014/0107439 A1* | 4/2014 | Atsumori | A61B 5/14551 600/558 |

(Continued)

FOREIGN PATENT DOCUMENTS

| | | |
|---|---|---|
| WO | 2012/165602 A1 | 12/2012 |
| WO | 2019008773 A1 | 1/2019 |
| WO | 2019009420 A1 | 1/2019 |

OTHER PUBLICATIONS

Office Action dated Jan. 10, 2022, in connection with corresponding Korean Application No. 10-2020-0011280 (11 pp., including machine-generated English translation).

(Continued)

*Primary Examiner* — Fabricio R Murillo Garcia
(74) *Attorney, Agent, or Firm* — Maier & Maier, PLLC (57) ABSTRACT

This brain activity feature amount extraction method includes acquiring a combination of a plurality of data items in order of higher effectiveness for discriminating whether a subject is a healthy person or a non-healthy person, among the plurality of data items, on the basis of the index value serving as the index indicating effectiveness or non-effectiveness for discriminating the group of healthy persons and the group of non-healthy persons from each other, and displaying the acquired combination of the plurality of data items in order of higher effectiveness.

12 Claims, 8 Drawing Sheets

(56) References Cited

U.S. PATENT DOCUMENTS

| | | | |
|---|---|---|---|
| 2014/0107494 A1* | 4/2014 | Kato | A61B 5/4088 600/300 |
| 2017/0231561 A1* | 8/2017 | Sutoko | G16H 10/20 702/19 |
| 2018/0338731 A1* | 11/2018 | Addison | A61B 5/02125 |
| 2020/0268304 A1 | 8/2020 | Yomota et al. | |
| 2021/0034912 A1* | 2/2021 | Lisi | G06T 7/0012 |
| 2022/0004913 A1 | 1/2022 | Nakae | |

OTHER PUBLICATIONS

Office Action dated May 31, 2022, in connection with corresponding Japanese Application No. 2019-029663 (8 pp., including machine-generated English translation).

Korean Office Action dated Apr. 22, 2021, in connection with corresponding KR Application No. 10-2020-0011280 (21pp., including machine-generated English translation).

Keum-Shik Hong, et al., "Feature Extraction and Classification Methods for Hybrid fNIRS-EEG Brain-Computer Interfaces", frontiers in Human Neuroscience, Review, vol. 12, Article 246, Jun. 28, 2018, pp. 1-25 (25pp.).

Fares Al-Shargie, et al., "Stress Assessment Based on Decision Fusion of EEG and fNIRS Signals", IEEE Access, vol. 5, Sep. 19, 2017, pp. 19889-19896 (8pp.).

Haleh Aghajani, et al., "Measuring Mental Workload with EEG+ fNIRS", frontiers in Human Neuroscience, Original Research, vol. 11, Article 359, Jul. 14, 2017, pp. 1-20 (20pp.).

Office Action dated Nov. 12, 2021 in Korea Patent Application No. 10-2020-0011280 with Computer-Generated English translation; 11 pgs.

\* cited by examiner

FEATURE AMOUNT 1-5: AVERAGE VALUE DIFFERENCE BETWEEN TASK AND REST

FEATURE AMOUNT 1: ENTIRE TASK AVERAGE VALUE − ENTIRE PRE-REST AVERAGE VALUE

| FIRST HALF PRE-REST | SECOND HALF PRE-REST | FIRST HALF TASK | SECOND HALF TASK | FIRST HALF POST-REST | SECOND HALF POST-REST |

FEATURE AMOUNT 2: ENTIRE TASK AVERAGE VALUE − (ENTIRE PRE-REST AVERAGE VALUE + ENTIRE POST-REST AVERAGE VALUE)/2

| FIRST HALF PRE-REST | SECOND HALF PRE-REST | FIRST HALF TASK | SECOND HALF TASK | FIRST HALF POST-REST | SECOND HALF POST-REST |

FEATURE AMOUNT 3: SECOND HALF TASK AVERAGE VALUE − SECOND HALF PRE-REST AVERAGE VALUE

| FIRST HALF PRE-REST | SECOND HALF PRE-REST | FIRST HALF TASK | SECOND HALF TASK | FIRST HALF POST-REST | SECOND HALF POST-REST |

FEATURE AMOUNT 4: SECOND HALF TASK AVERAGE VALUE − (SECOND HALF PRE-REST AVERAGE VALUE + SECOND HALF POST-REST AVERAGE VALUE)/2

| FIRST HALF PRE-REST | SECOND HALF PRE-REST | FIRST HALF TASK | SECOND HALF TASK | FIRST HALF POST-REST | SECOND HALF POST-REST |

FEATURE AMOUNT 5: SECOND HALF TASK AVERAGE VALUE − SECOND HALF PRE-REST AVERAGE VALUE

| FIRST HALF PRE-REST | SECOND HALF PRE-REST | FIRST HALF TASK | SECOND HALF TASK | FIRST HALF POST-REST | SECOND HALF POST-REST |

| | p-value | Youden-Index | Task | Channel | Signal | Feature-type | Feature-combi | Trial |
|---|---|---|---|---|---|---|---|---|
| 1 | 1.53E-05 | 0.554286 | Sumanu | Channel-43 | Oxyhb | Feature11 | Single | Trial-3 |
| 2 | 2.75E-05 | 0.605714 | Reikan | Channel-52 | Deoxyhb | Feature11 | Diff | Trial-2x4 |
| 3 | 4.02E-05 | 0.514286 | Sumanu | Channel-43 | Totalxyhb | Feature11 | Single | Trial-3 |
| 4 | 5.15E-05 | 0.554286 | Sumanu | Channel-44 | Deoxyhb | Feature5 | Diff | Trial-3x4 |
| 5 | 5.48E-05 | 0.56 | Keisan | Channel-19 | Oxyhb | Feature4 | Single | Trial-4 |
| 6 | 5.82E-05 | 0.542857 | Kuukan | Channel-7 | Oxyhb | Feature11 | Diff | Trial-1x3 |
| 7 | 6.58E-05 | 0.52 | Keisan | Channel-24 | Deoxyhb | Feature2 | Diff | Trial-1x3 |
| 8 | 6.58E-05 | 0.514286 | Sumanu | Channel-9 | Deoxyhb | Feature21 | Single | Trial-4 |
| 9 | 7.43E-05 | 0.531429 | Kuukan | Channel-13 | Deoxyhb | Feature11 | Diff | Trial-2x3 |
| 10 | 7.89E-05 | 0.491429 | Reikan | Channel-51 | Deoxyhb | Feature3 | Diff | Trial-1x2 |
| 11 | 8.89E-05 | 0.605714 | Keisan | Channel-24 | Oxyhb | Feature1 | Diff | Trial-1x3 |
| 12 | 8.89E-05 | 0.457143 | Kuukan | Channel-5 | Oxyhb | Feature11 | Diff | Trial-1x3 |
| 13 | 0.0001 | 0.485714 | Kuukan | Channel-41 | Deoxyhb | Feature11 | Diff | Trial-1x3 |
| 14 | 0.000106 | 0.411429 | Reikan | Channel-28 | Deoxyhb | Feature4 | Ratio | Trial-3x4 |
| 15 | 0.000113 | 0.531429 | Keisan | Channel-24 | Oxyhb | Feature5 | Diff | Trial-1x3 |
| 16 | 0.000113 | 0.497143 | Sumanu | Channel-33 | Oxyhb | Feature11 | Single | Trial-3 |
| 17 | 0.000113 | 0.462857 | Sumanu | Channel-24 | Totalxyhb | Feature11 | Single | Trial-3 |
| 18 | 0.00012 | 0.468571 | Sumanu | Channel-45 | Oxyhb | Feature11 | Single | Trial-3 |
| 19 | 0.000127 | 0.485714 | Kuukan | Channel-46 | Deoxyhb | Feature3 | Diff | Trial-3x4 |
| 20 | 0.000134 | 0.485714 | Sumanu | Channel-49 | Deoxyhb | Feature21 | Single | Trial-1 |

BRAIN ACTIVITY FEATURE AMOUNT EXTRACTION METHOD

CROSS-REFERENCE TO RELATED APPLICATIONS

Priority is claimed on Japanese Patent Application No. 2019-029663, filed Feb. 21, 2019, by Satoshi Yomota, Shin Nakamura, Kenta Chinomi, and Nobuyuki Akinaga and entitled brain activity feature amount extraction method and the content of which is incorporated herein by reference.

FIELD

The present invention relates to a brain activity feature amount extraction method, and particularly to a brain activity feature amount extraction method including a step of acquiring a feature amount relating to a change in cerebral blood flow rate.

BACKGROUND

In the related art, brain activity feature amount extraction methods, including a step of acquiring a feature amount relating to a change in cerebral blood flow rate, are known. Such a brain activity feature amount extraction method is disclosed in, for example, International Publication No. 2012/165602.

A cognitive dysfunction discrimination apparatus, which measures cerebral blood flow data of a subject under the execution of cognitive assignment using near-infrared spectroscopy, is disclosed in International Publication No. 2012/165602. The cognitive dysfunction discrimination apparatus of International Publication No. 2012/165602 is configured to give various cognitive assignments to the subject to perform extraction of a plurality of feature amounts with respect to the cerebral blood flow data obtained by measuring a plurality of measurement regions by functional near-infrared spectroscopy (fNIRS) and perform discrimination of the cognitive function of the subject with the extracted feature amounts and pre-built models used for determination of the cognitive dysfunction.

In the cognitive dysfunction discrimination apparatus of International Publication No. 2012/165602, the feature amounts of the cerebral blood flow data under the execution of the cognitive assignments are acquired for the subject who has already known whether or not there is an impairment in the cognitive function, and the models used for the determination of the cognitive dysfunction are built on the basis of the acquired feature amounts. In the cognitive dysfunction discrimination apparatus of International Publication No. 2012/165602, when the models used for the determination of the cognitive dysfunction are built, feature amounts useful for determination criteria for discriminating a group of healthy persons and a group of non-healthy persons (cognitive function disabled persons) are selected by a sequential selection method. In addition, an average value of estimated correct answer rates of the two respective groups (the group of healthy persons and the group of non-healthy persons) is used as a feature selection criterion of the sequential selection method. Also, in International Publication No. 2012/165602, as the feature amounts (determination criteria) for performing discrimination between the group of healthy person and the group of non-healthy person (cognitive function disabled persons), a total of twelve feature amounts of feature amounts in regions on the right-hand side of the prefrontal cortex including seven measurement regions and feature amounts in regions behind the left temporal lobe including five measurement regions are selected.

However, in the cognitive dysfunction discrimination apparatus described in International Publication No. 2012/165602, it is considered that the selected feature amounts may be relatively limited because the feature amounts useful for the determination criteria for discriminating the group of healthy persons and the group of non-healthy persons are selected by the sequential selection method of selecting the feature amounts according to certain rules. For this reason, a problem that whether a subject is a healthy person or a non-healthy person cannot be appropriately discriminated due to the extraction omission of the feature amounts (determination criteria) useful for discriminating the group of healthy persons and the group of cognitive function disabled persons is considered.

SUMMARY

The invention has been made in order to solve the above problems, and an object of this invention is to provide a brain activity feature amount extraction method capable of suppressing a situation in which it is not possible to appropriately discriminate whether a subject is a healthy person or a non-healthy person due to the extraction omission of useful determination criteria.

In order to achieve the above object, a brain activity feature amount extraction method in one aspect of this invention includes a step of giving an assignment for triggering brain activity to a subject including a group of healthy persons and a group of non-healthy persons; a step of measuring a change in a cerebral blood flow rate for each measurement region of the subject when the assignment is given to the subject; a step of acquiring a feature amount relating to the change in the cerebral blood flow rate; a step of calculating an index value serving as an index indicating effectiveness or non-effectiveness for discriminating the group of healthy persons and the group of non-healthy persons from each other with respect to a set of the assignment, the measurement region, and the feature amount; a step of acquiring a plurality of data items in which the set of the assignment, the measurement region, and the feature amount is associated with the calculated index value; a step of acquiring a combination of the plurality of data items in order of higher effectiveness for discriminating whether the subject is a healthy person or a non-healthy person, among the plurality of data items on the basis of the calculated index value; and a step of displaying the acquired combination of the plurality of data items in order of higher effectiveness.

As described above, the brain activity feature amount extraction method according to this invention includes the step of acquiring the combination of the plurality of data items in order of higher effectiveness for discriminating whether the subject is a healthy person or a non-healthy person among the plurality of data items associated with the index value on the basis of the index value serving as the index indicating effectiveness or non-effectiveness for discriminating the group of healthy persons and the group of non-healthy persons from each other, and the step of displaying the acquired combination of the plurality of data items in order of higher effectiveness. Accordingly, the plurality of data items associated with the index value are displayed in order of higher effectiveness for discriminating whether the subject is a healthy person or a non-healthy person. Thus, the plurality of data items associated with the index value with high effectiveness can be easily ascertained. As a result, the occurrence of extraction omission of the feature amount (determination criteria) useful for discriminating whether a subject is a healthy person or a non-healthy person can be suppressed. Thus, a situation in which whether the subject is a healthy person or a non-healthy person cannot be appropriately discriminated due to the extraction omission of the useful determination criteria can be suppressed.

The brain activity feature amount extraction method according to the above one aspect preferably further includes a step of creating a plurality of models with different numbers of the data items with respect to the displayed combination of the plurality of data items, and acquiring the number of the data items required to discriminate whether the subject is the healthy person or the non-healthy person on the basis of a correct answer rate of each of the plurality of created models. If the invention is configured in this way, the number of the data items required (in acquisition and display) to discriminate whether the subject is a healthy person or a non-healthy person can be easily discriminated on the basis of the correct answer rates of the plurality of models with different numbers of the data items.

In a configuration in which the number of the data items required to discriminate whether the subject is a healthy person or a non-healthy person is acquired, preferably, the step of acquiring the number of the data items further includes a step of creating a plurality of regression models with different numbers of the plurality of data items, and acquiring the number of the data items required to discriminate whether the subject is the healthy person or the non-healthy person on the basis of a correct answer rate of each of the plurality of created regression models. If the invention is configured in this way, the number of the data items required to discriminate whether the subject P is a healthy person or a non-healthy person can be easily acquired on the basis of the correct answer rate of each of the plurality of regression models.

In a configuration in which the number of the data items required to discriminate whether the subject is a healthy person or a non-healthy person is acquired, preferably, the step of acquiring the number of the data items includes a step of acquiring the number of the data items in which the correct answer rate is equal to or more than a predetermined threshold. If the invention is configured in this way, the number of the data items required to discriminate whether the subject is a healthy person or a non-healthy person can be easily determined on the basis of the predetermined threshold.

The brain activity feature amount extraction method according to the above one aspect preferably further includes a step of rearranging the plurality of data items associated with the index value in order of higher effectiveness. If the invention is configured in this way, the acquired combination of the plurality of data items can be easily displayed in order of higher effectiveness.

In the brain activity feature amount extraction method according to the above one aspect, preferably, the step of acquiring the feature amount relating to the change in the cerebral blood flow rate includes a step of changing a period in which an average value of the change in the cerebral blood flow rate is acquired, and acquiring at least one of a plurality of kinds of average values of changes in the cerebral blood flow rate acquired on the basis of an average value of the change in the cerebral blood flow rate in a predetermined period included in a period in which the assignment is performed and an average value of the change in the cerebral blood flow rate in a predetermined period included in a period in which the assignment is not performed, as the feature amount relating to the change in the cerebral blood flow rate. If the invention is configured in this way, the feature amount relating to the change in the cerebral blood flow rate can be acquired from any of the plurality of kinds of the average values of the changes in the cerebral blood flow rate. Thus, the number of the plurality of data items for discriminating the group of healthy persons and the group of non-healthy persons from each other can be effectively increased. As a result, it is possible to acquire a more sufficient number of determination criteria for discriminating whether the subject is a healthy person or a non-healthy person.

In the brain activity feature amount extraction method according to the above one aspect, preferably, the step of acquiring the feature amount relating to the change in the cerebral blood flow rate includes a step of acquiring at least one of the area center of gravity of a region formed by a curved line showing the change in the cerebral blood flow rate in a period where the assignment is performed or a maximum value of a gradient in the curved line showing the change in the cerebral blood flow rate as the feature amount relating to the change in the cerebral blood flow rate. If the invention is configured in this way, for example, there is a case where area centers of gravity or maximum values of the gradient are different even if average values of changes in the cerebral blood flow rate in a certain period are the same. Thus, whether the subject is a healthy person or a non-healthy person can be accurately discriminated by including at least one of the area center of gravity or the maximum value of the gradient included as the feature amount relating to the change in the cerebral blood flow rate.

In the brain activity feature amount extraction method according to the above one aspect, preferably, the step of giving the assignment includes a step of giving a plurality of the assignments with different difficulty degrees in the same assignment, and the step of acquiring the feature amount relating to the change in the cerebral blood flow rate includes a step of acquiring a difference or a ratio of average values of the cerebral blood flow rates between periods in which the plurality of assignments with different difficulty degrees are performed as the feature amount. Here, in the measurement of cerebral blood flow data when a cognitive assignment is executed, each subject is subjected to biases, such as habit, experience, education level to an assignment. Hence, since the execution of the cognitive assignment with a constant difficulty degree with respect to subjects is too easy for a certain subject, brain activity may not be detected, and since this execution is too difficult for a certain subject, the execution of the assignment may be given up. Thus, by configuring the invention as described above, changes in the brain activity caused by assignment difficulty degrees according to the subjects can be measured. Thus, even when there are individual differences in adaptation of the subjects to the cognitive assignments, the degree of the cognitive function can be determined.

In the brain activity feature amount extraction method according to the above one aspect, preferably, the step of giving the assignment includes a step of giving at least one of sensory stimulation, calculation, memory, imagination, and spatial cognition for the subject as the assignment to the subject. If the invention is configured in this way, the plurality of kinds of assignments that trigger the brain activity is triggered can be given to the subject. Thus, the number of the plurality of data items for discriminating the group of healthy persons and the group of non-healthy persons from each other can be effectively increased. As a result, it is possible to acquire a further sufficient number of determination criteria for discriminating whether the subject is a healthy person or a non-healthy person.

In the brain activity feature amount extraction method according to the above one aspect, preferably, the step of measuring the change in the cerebral blood flow rate includes, as the index of the change in the cerebral blood flow rate, a step of measuring at least one of a change in an amount of oxygenated hemoglobin, a change in an amount of deoxygenated hemoglobin, and, a change in a total amount of hemoglobin that is a total amount of the amount of oxygenated hemoglobin and the amount of deoxygenated hemoglobin. If the invention is configured in this way, the change in the cerebral blood flow rate of the subject can be acquired by the plurality of kinds of indexes. Thus, the number of the plurality of data items for discriminating the group of healthy persons and the group of non-healthy persons from each other can be effectively increased. As a result, it is possible to acquire a further sufficient number of determination criteria for discriminating whether the subject is a healthy person or a non-healthy person. In addition, the amount of oxygenated hemoglobin may relatively sensitively react on the assignment, while sensitively reacting on factors, such as the body motion of the subject, other than the assignment. As a result, there is a case where noise is included in a measurement result. On the other hand, since the amount of deoxygenated hemoglobin is insensitive to the body motion of the subject (is accurate with respect to localization of a brain activity region), a measurement result with relatively little noise can be obtained by using the amount of deoxygenated hemoglobin as the index of the change in the cerebral blood flow rate.

In the brain activity feature amount extraction method according to the above one aspect, preferably, the step of measuring the change in the cerebral blood flow rate of each measurement region includes a step of measuring a change in the cerebral blood flow rate for each measurement region set to a range including at least one of F3, F4, P3, and P4 of the international 10-20 method. If the invention is configured in this way, changes in the cerebral blood flow rate of ranges (the frontal association cortex, the motor cortex, the interval cortex) generally used when brain waves are measured can be measured. Thus, the change in the cerebral blood flow rate with respect to the assignment can be appropriately measured.

In the brain activity feature amount extraction method according to the above one aspect, preferably, the step of measuring the change in the cerebral blood flow rate for each measurement region further includes a step of measuring the change in the cerebral blood flow rate for each measurement region by the near-infrared spectroscopy (NIRS). If the invention is configured in this way, the change in the cerebral blood flow rate of the subject can be measured using the NIRS apparatus. As a result, the NIRS apparatus is non-invasive, and does not need a large-scale facility as compared to magnetic resonances imaging (MRI) or the like. Thus, the change in the cerebral blood flow rate of the subject can be simply measured. In addition, the NIRS apparatus is an apparatus that is mounted on the head of the subject and measures the change in the cerebral blood flow rate by measuring a change in the amount of hemoglobin in a cerebral blood vessel of the subject with near-infrared light.

DETAILED DESCRIPTION

Hereinafter, an embodiment in which the present invention is embodied will be described with reference to the drawings.

First, the configuration of a brain activity measurement system 100 for carrying out a brain activity feature amount extraction method according to an embodiment of the present invention will be described with reference to FIGS. 1 to 3.

(Configuration of Brain Activity Measurement System)

Figure 1:
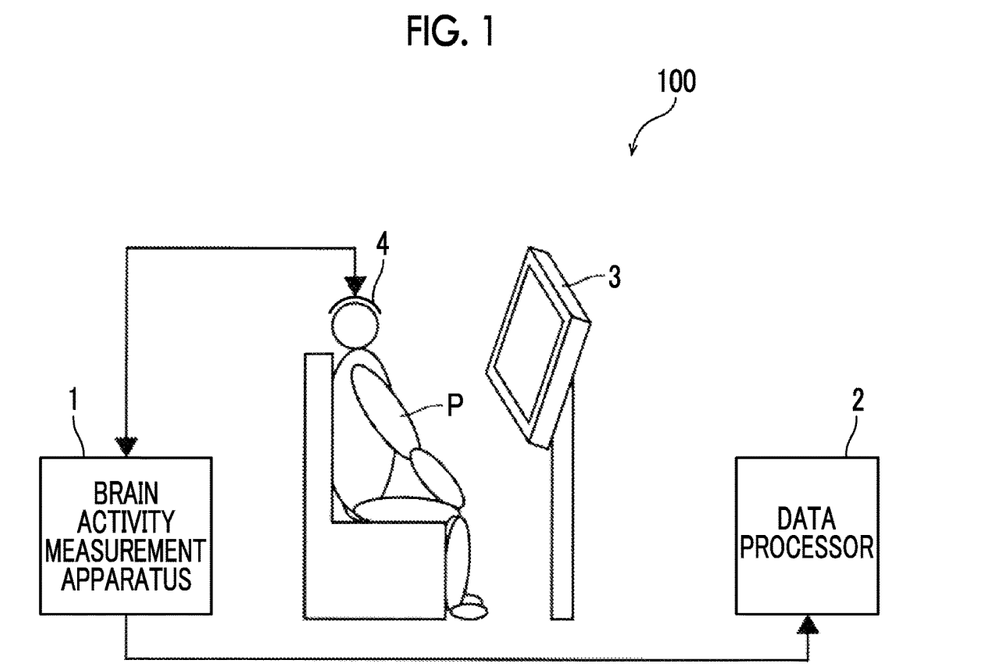
FIG. 1 is a view for illustrating an entire configuration of a brain activity measurement system for carrying out a brain activity feature amount extraction method according to an embodiment of the present invention.

As illustrated in FIG. 1, the brain activity measurement system 100 includes a brain activity measurement apparatus 1, a data processor 2, and a display device 3.

The brain activity measurement apparatus 1 is an apparatus (optical measurement apparatus) that optically measures the brain activity of a subject P by using near-infrared spectroscopy (NIRS) and generates time-series measurement result data. Specifically, the brain activity measurement apparatus 1 is an NIRS apparatus. The brain activity measurement apparatus 1 radiates measurement light in a wavelength region of near-infrared light from a light-sending probe (not illustrated) disposed on the head surface of the subject P. Then, the intensity (the amount of light received) of the measurement light is acquired by causing the measurement light reflected within the head to enter a light-receiving probe (not illustrated) disposed on the head surface to detect the measurement light. A plurality of the light-sending probes and the light-receiving probes are provided, respectively, and are attached to a holder 4 for fixing the respective probes to predetermined positions on the head surface. In the present embodiment, the brain activity measurement apparatus 1 measures the change amounts of oxygenated hemoglobin, deoxygenated hemoglobin, and total hemoglobin on the basis of the intensity (amount of light received) of the measurement light with a plurality of wavelengths (for example, three wavelengths, 780 nm, 805 nm, and 830 nm), and the light absorption characteristics of hemoglobin, as indexes of changes in cerebral blood flow rate.

The data processor 2 performs statistical processing of the measurement data sent from the brain activity measurement apparatus 1. That is, the data processor 2 is configured to calculate statistical data for determining the grade of the cognitive function of the subject P. The data processor 2 is constituted of a personal computer (PC) including a CPU, a memory, a hard disk drive, and the like.

The display device 3 is configured to display tasks (refer to FIG. 4) caused to be executed by the subject P. The display device 3 is a monitor, such as a liquid crystal display. In addition, the tasks are examples of an "assignment" of the claims.

Figure 2:
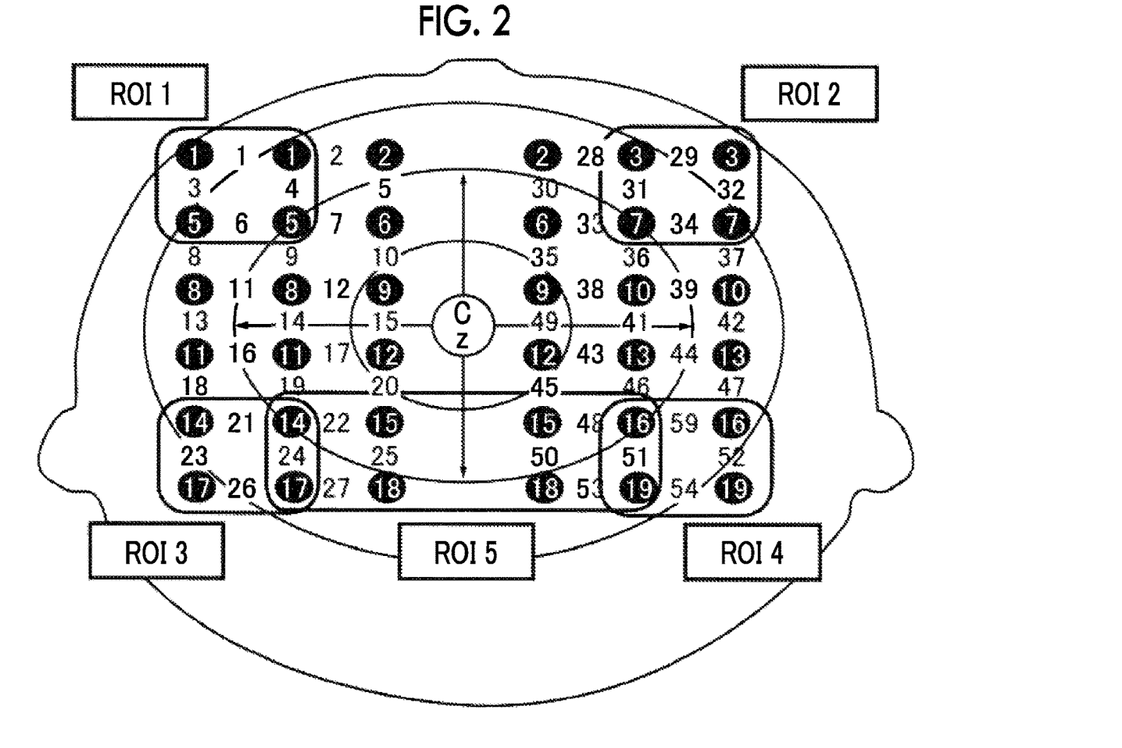
FIG. 2 is a schematic view illustrating measurement regions when measuring brain activity according to the embodiment of the present invention.

FIG. 2 illustrates measurement regions when the blood flow rate of the brain of the subject P is measured by the brain activity measurement apparatus 1. Additionally, FIG. 3 is a view illustrating measurement regions in the international 10-20 method. In the brain activity measurement apparatus 1, the measurement regions when the measurement data of the brain activity of the subject P is acquired are set to ranges including F3, F4, P3, and P4 of the international 10-20 method illustrated in FIG. 3. Specifically, 54 channels as illustrated in FIG. 2 are set to the measurement regions as the ranges including any of F3, F4, P3, and P4 of the international 10-20 method. In that case, ROI1 to ROI5 are set as regions of interest (ROI).

(Brain Activity Feature Amount Extraction Method)

Next, the brain activity feature amount extraction method of the present embodiment of acquiring the combination and number of a plurality of data items for discriminating whether the subject P is a healthy person or a non-healthy person will be described with reference to FIGS. 4 to 7.

Figure 4:
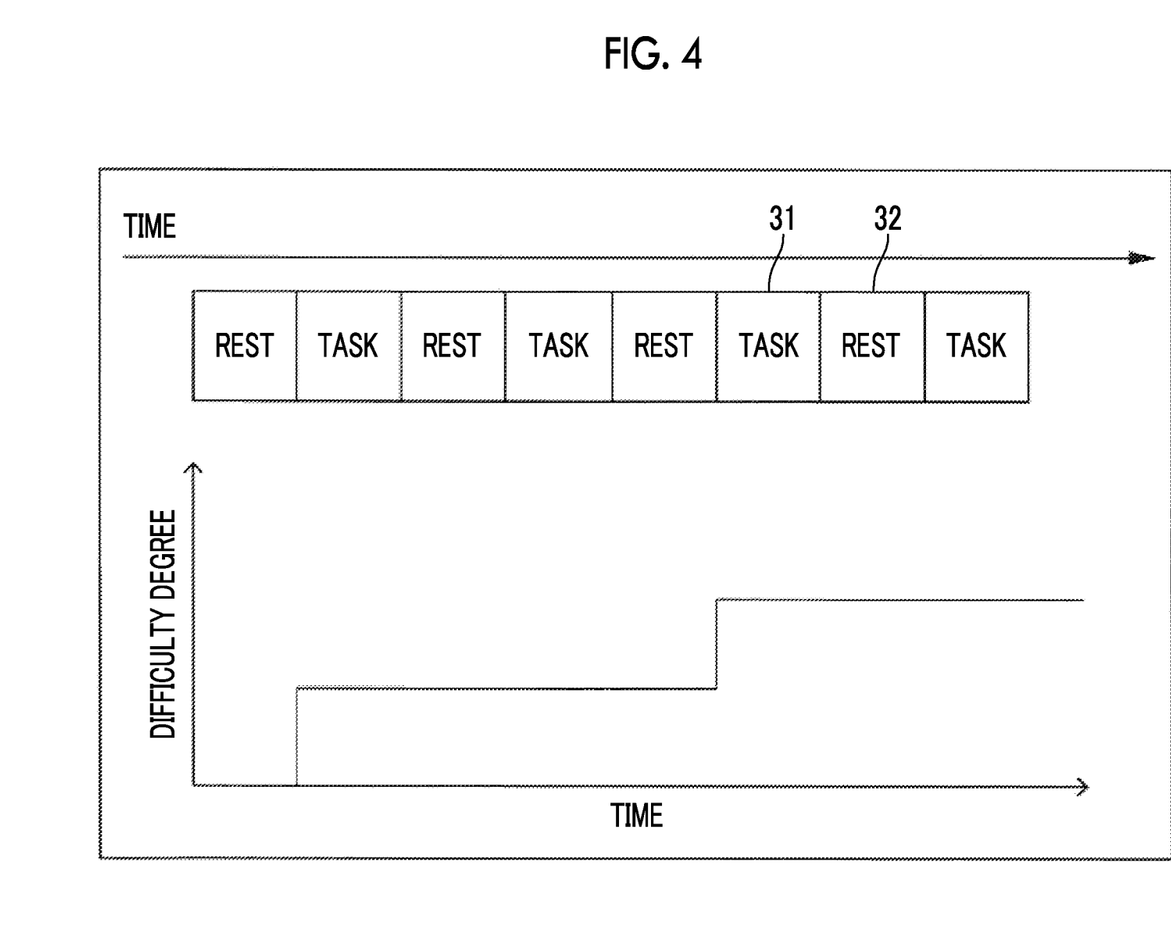
FIG. 4 is a timing chart of task periods and rest periods according to the embodiment of the present invention, and a graph illustrating time changes in task intensity.
Figure 8:
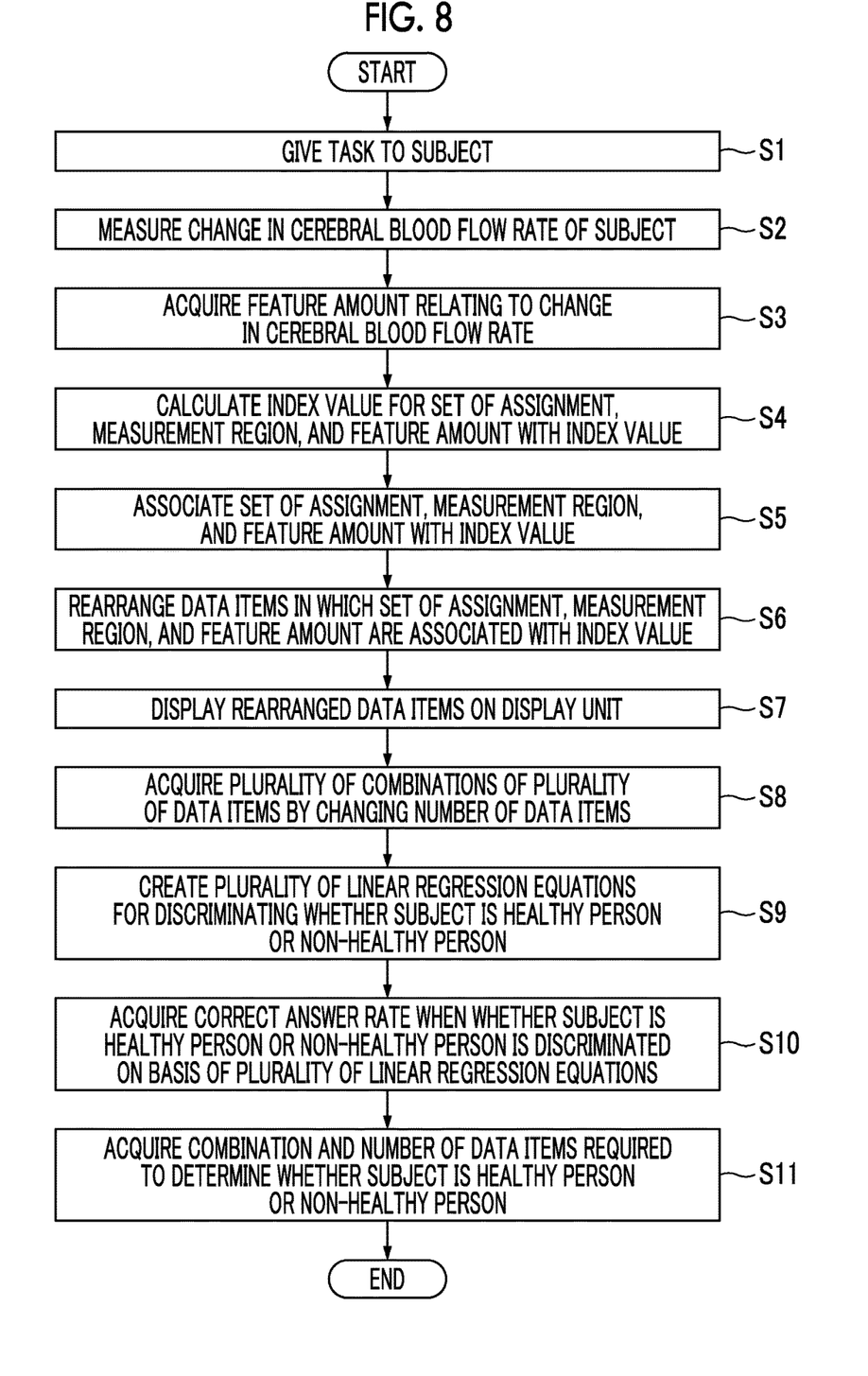
FIG. 8 is a flowchart illustrating a flow for acquiring a combination of a plurality of data items for discriminating whether a subject is a healthy person or a non-healthy person.

As illustrated in FIG. 4, in the brain activity feature amount extraction method of the present embodiment, a task for triggering brain activity is given to the subject P including a group of healthy persons and a group of non-healthy persons (refer to Step S1 of FIG. 8). Specifically, as illustrated in a timing chart of FIG. 4, when a task is given, a plurality of times of the tasks are given to the subject P. Additionally, in a case where the plurality of times of tasks are given to the subject P, a task period 31 in which a task is given to the subject P and a rest period 32 in which a task is not given to the subject P are alternately repeated. The task period 31 is, for example, for 15 seconds. Additionally, the rest period 32 is, for example, for 30 seconds. In the rest period 32, a baseline when a change in the cerebral blood flow rate of the subject P is measured is created by causing the subject P to pronounce meaningless words. The meaningless words caused to be pronounced by the subject P in the rest period 32 are, for example, "a, i, u, e, o". In addition, an example in which the task is repeated four times is illustrated in FIG. 4.

In addition, in the brain activity feature amount extraction method of the present embodiment, when a task is given (refer to Step S1 illustrated in FIG. 8), sensory stimulation, calculation, memory, imagination, and spatial cognition for the subject P are given to the subject P as tasks. Specifically, when a task given to the subject P is the sensory stimulation, the sensory stimulation is given to a sensory organ of the subject P. For example, cold sensory stimulation is given to the subject P by applying a cold pack to the palm of the subject P. Additionally, when a task given to the subject P is the calculation, a calculation problem is given to the subject P. For example, the serial seven (100−7) used for the mini-mental state examination (MMSE) for diagnosis of dementia is used as the calculation problem. In addition, the serial seven (100−7) is a problem in which 7 is consecutively subtracted from 100. Additionally, in a case where tasks given to the subject P are memory and imagination, an experimenter who carries out the brain activity feature amount extraction method writes similar letters on a hand of the subject P, and gives a problem in which the subject P guesses the letters is given. The similar letters are, for example, "su", "ma", and "nu". Additionally, in a case where a task given to the subject P is the spatial cognition, a landscape photograph is displayed on the display device 3, a map in which buildings drawn on the landscape photograph are illustrated as a schematic view is passed to the subject P, and a problem of answering where to stand to see the landscape of the landscape photograph with a number is given.

Additionally, in the brain activity feature amount extraction method of the present embodiment, when a task is given (refer to Step S1 illustrated in FIG. 8), a plurality of tasks with different difficulty degrees in the same task are given. Specifically, as illustrated in a timing chart of FIG. 4, the tasks are given to the subject P such that the difficulty degrees of third and fourth tasks are higher than the difficulty degrees of first and second tasks. For example, in a case where the calculation problem is given to the subject P, in the first and second tasks, the problem of consecutively subtracting 7 from 100 is given to the subject P, and in the third and fourth tasks, a problem of consecutively subtracting 3 from 100, having higher difficulty degrees than the problem of consecutively subtracting 7 from 100, is given to the subject P. In addition, in the subtraction of even numbers and subtraction of odd numbers, the subtraction of odd numbers has a higher difficulty degree. Additionally, when the experimenter writes the similar letters on the hand of the subject P and the problem in which the subject P guesses the letters is given, letters written on the hand of the subject P are one letter in the first and second tasks, and letters written on the hand of the subject P are two letters in the third and fourth tasks. Additionally, in a case where the landscape photograph is displayed on the display device 3, the map in which buildings drawn on the landscape photograph are illustrated as a schematic view is passed to the subject P, and the problem of answering where to stand to see the landscape of the landscape photograph with a number is given, for example, in the third and fourth tasks, the difficulty degrees of the tasks are made higher by increasing the number of roads or buildings than in the first and second tasks.

Additionally, in the brain activity feature amount extraction method of the present embodiment, when a task is given to the subject P, a change in the cerebral blood flow rate for each measurement region of the subject P is measured (refer to Step S2 illustrated in FIG. 8). In detail, when the change in the cerebral blood flow rate is measured, a change in the amount of oxygenated hemoglobin, a change in the amount of deoxygenated hemoglobin, and, a change in the total amount of hemoglobin that is a total amount of the amount of oxygenated hemoglobin and the amount of deoxygenated hemoglobin are measured as indexes of the change in the cerebral blood flow rate.

Figure 3:
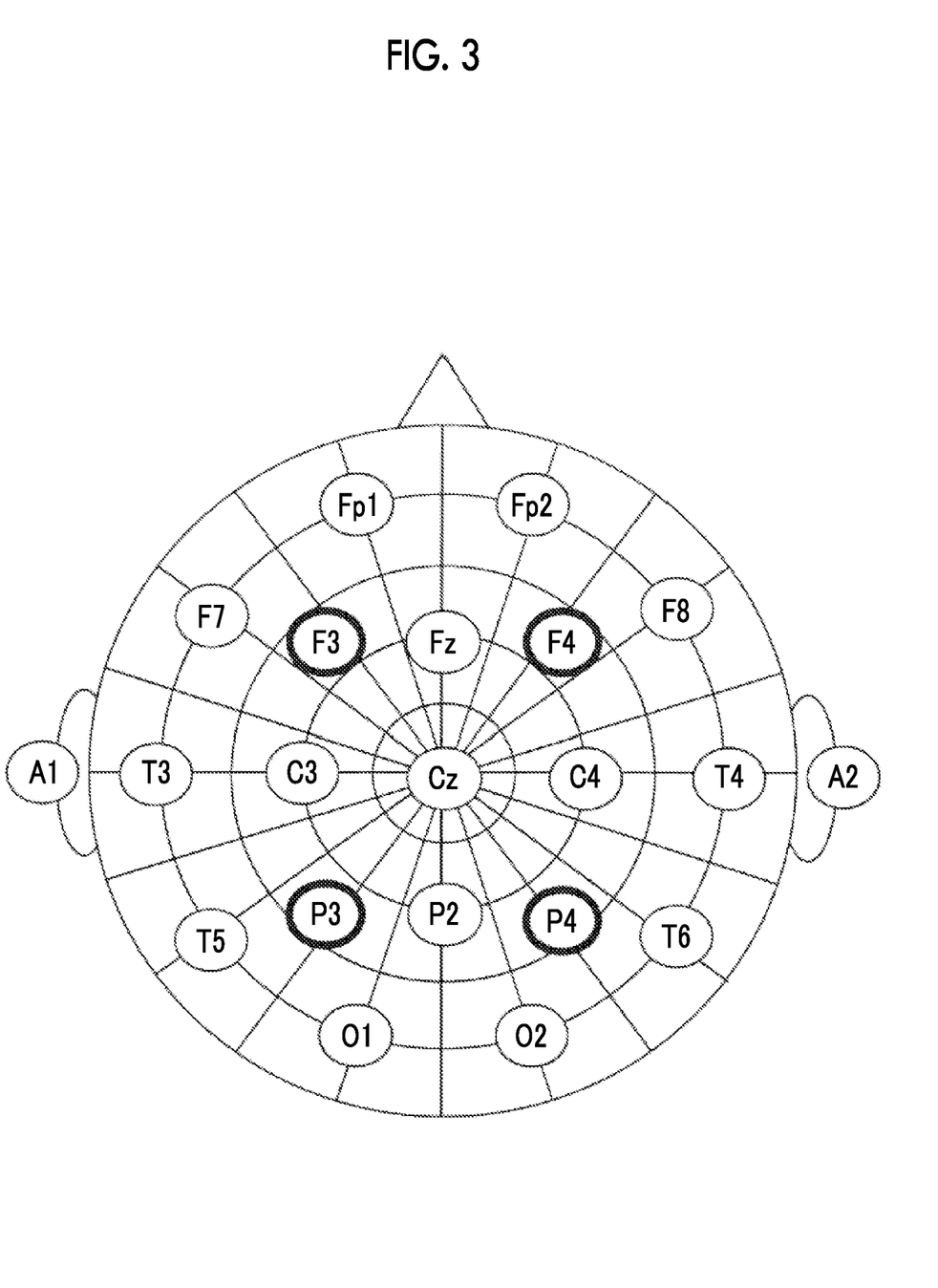
FIG. 3 is a schematic view for illustrating measurement regions of the international 10-20 method.
Figure 5A:
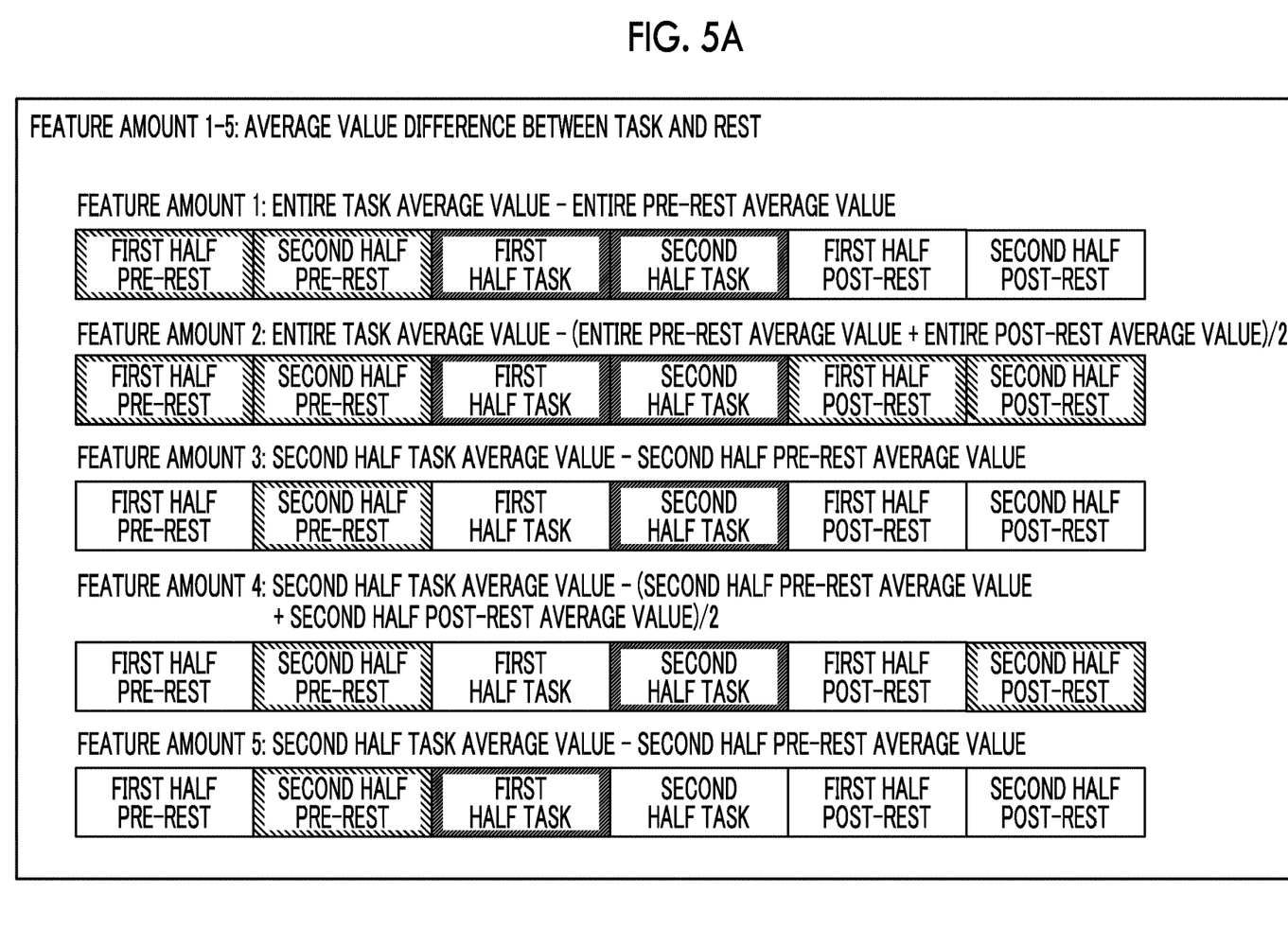
FIG. 5A is a view for illustrating feature amounts (average value differences between tasks and rests) in the brain activity feature amount extraction method according to the embodiment of the present invention.
Figure 5B:
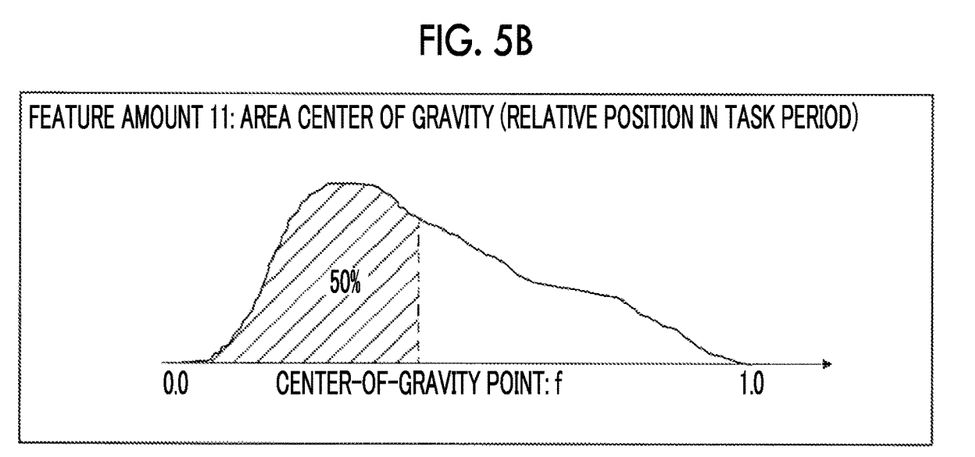
FIG. 5B is a view for illustrating another feature amount (area center of gravity) in the brain activity feature amount extraction method according to the embodiment of the present invention.
Figure 5C:
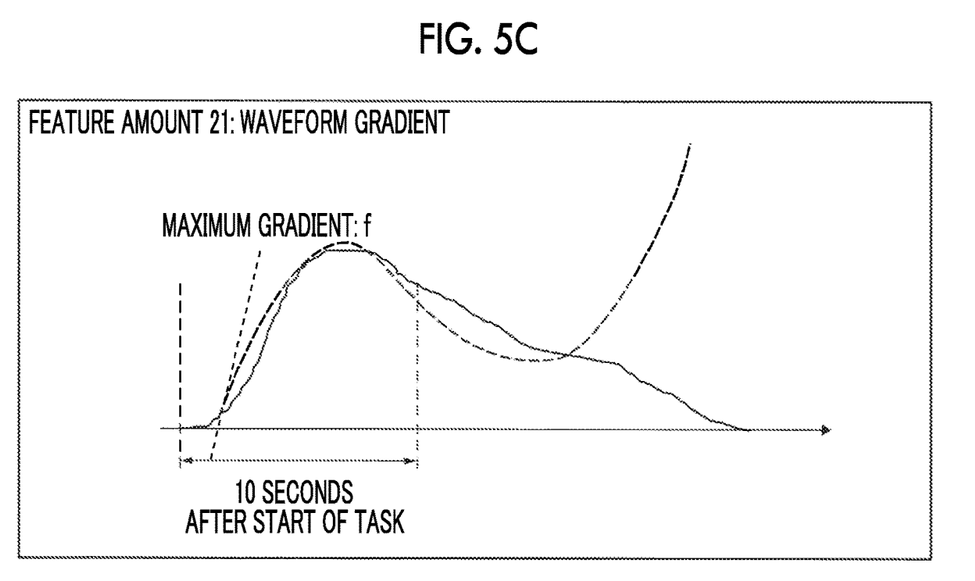
FIG. 5C is a view for illustrating still another feature amount (waveform gradient) in the brain activity feature amount extraction method according to the embodiment of the present invention.

Additionally, as illustrated in FIGS. 2 and 3, when the change in the cerebral blood flow rate is measured, changes in the cerebral blood flow rate for the respective measurement regions set as the ranges including F3, F4, P3, and P4 of the international 10-20 method are measured. Additionally, when the change in the cerebral blood flow rate is measured, the change in the cerebral blood flow rate for each measurement region is measured by the near-infrared spectroscopy (NIRS) as described above. Additionally, as illustrated in FIGS. 5A to 5C, in the brain activity feature amount extraction method of the present embodiment, feature amounts relating to the change in the cerebral blood flow rate are acquired (refer to Step S3 of FIG. 8). In detail, as illustrated in FIG. 5A, when the feature amounts relating to the change in the cerebral blood flow rate are acquired, a period in which an average value of the change in the cerebral blood flow rate is changed, and a plurality of kinds of average values of changes in the cerebral blood flow rate acquired on the basis of an average value of a change in the cerebral blood flow rate included in a predetermined period included in the task period 31 and an average value of a change in the cerebral blood flow rate included in a predetermined period included in the rest period 32 are acquired as the feature amounts relating to the change in the cerebral blood flow rate. Additionally, as illustrated in FIGS. 5B and 5C, when the feature amounts relating to the change in the cerebral blood flow rate are acquired, the area center of gravity of a region formed by a curved line showing the change in the cerebral blood flow rate in the task period 31 (refer to FIG. 5B) and a maximum value of a gradient in the curved line showing the change in the cerebral blood flow rate (refer to view 5C) are acquired as the feature amounts relating to the change in the cerebral blood flow rate.

Specifically, as illustrated in FIG. 5A, feature amounts 1 to 5 are acquired as the feature amounts relating to the change in the cerebral blood flow rate. The feature amount 1 is a difference between an average value of a change in the cerebral blood flow rate in the entire task period 31 (refer to FIG. 4) and an average value of a change in the cerebral blood flow rate in the entire rest period 32 (refer to FIG. 4) immediately before the task period 31. The feature amount 2 is a difference between the average value of the change in the cerebral blood flow rate of the entire task period 31 and a value obtained by averaging the average value of the change in the cerebral blood flow rate of the entire rest period 32 immediately before the task period 31 and an average value of a change in the cerebral blood flow rate of the entire rest period 32 immediately after the task period 31. The feature amount 3 is a difference between an average value of a change in the cerebral blood flow rate in the second half of the task period 31 and an average value of a change in the cerebral blood flow rate in the second half of the rest period 32 immediately before of the task period 31. The feature amount 4 is a difference between the average value of the change in the cerebral blood flow rate in the second half of the task period 31 and a value obtained by averaging the average value of the change in the cerebral blood flow rate in the second half of the rest period 32 immediately before the task period 31 and an average value of a change in the cerebral blood flow rate in the second half of the rest period 32 immediately after the task period 31. The feature amount 5 is a difference between an average value of a change in the cerebral blood flow rate in the first half of the task period 31 and the average value of the change in the cerebral blood flow rate in the second half of the rest period 32 immediately before of the task period 31. That is, the feature amount 5 is a change in the (rising) cerebral blood flow rate immediately after a task is given to the subject P.

Additionally, as illustrated in FIGS. 5B and 5C, the feature amount 11 and the feature amount 21 are acquired as the feature amounts relating to the change in the cerebral blood flow rate, respectively. The feature amount 11 shows a relative position (center-of-gravity point f) in the task period 31 including the position of the area center of gravity of a region formed by the curved line showing the change in the cerebral blood flow rate in the task period 31 (refer to FIG. 4). In addition, since the feature amount 11 is not easily influenced by the absolute value of the cerebral blood flow rate unlike the feature amounts 1 to 5 on the basis of an average value of a change in the cerebral blood flow rate in a predetermined period, the feature amount 11 is not easily influenced by optical path lengths at the time of different measurement due to differences between subjects P or the measurement regions. The feature amount 21 is a gradient in a case where the gradient becomes maximum within 10 seconds after the start of the task period 31, in the curved line showing the change in the cerebral blood flow rate in the task period 31.

Figure 6:
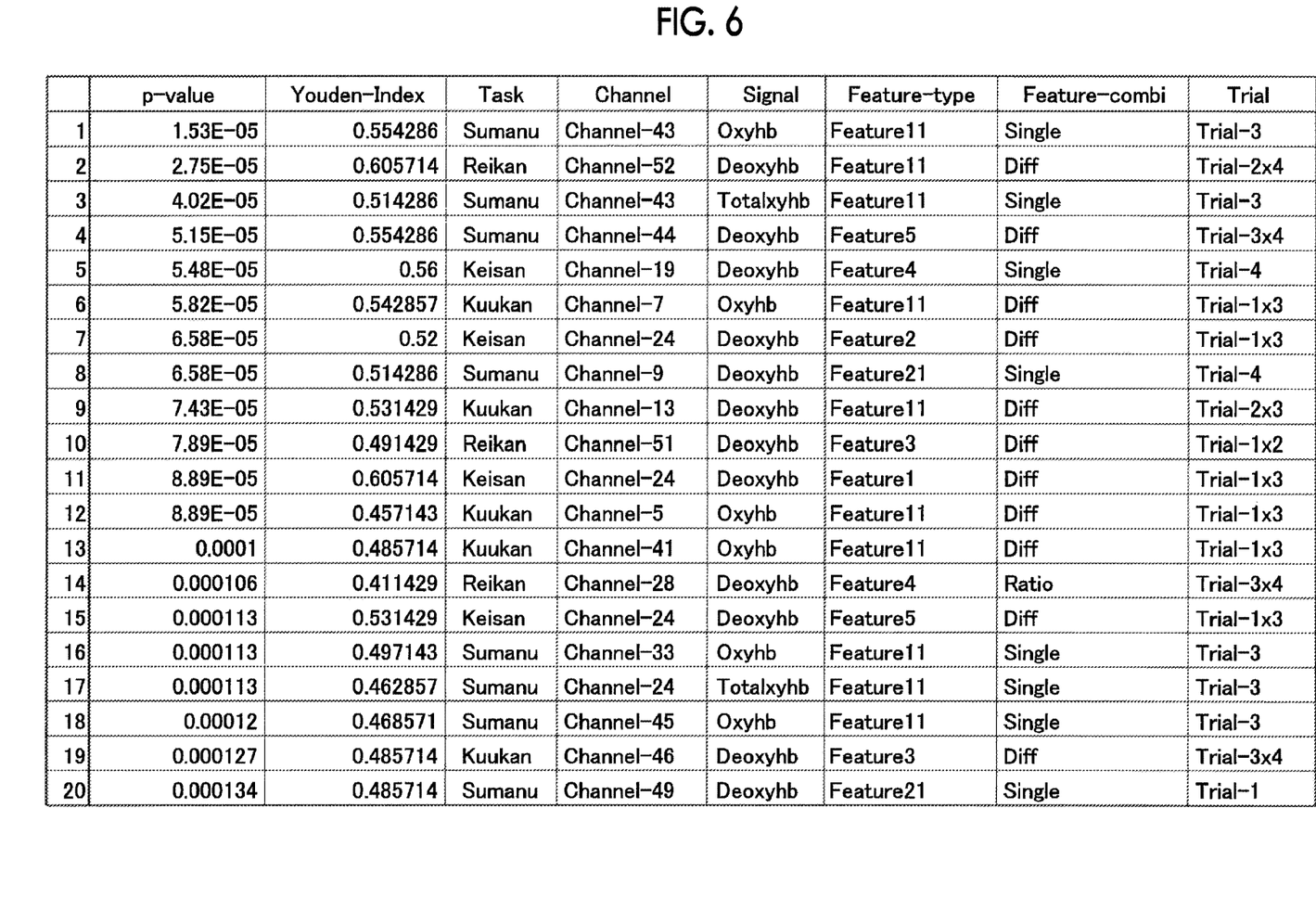
FIG. 6 is a view for illustrating a plurality of data items in which assignments, measurement regions, and feature amounts are associated with index values for discriminating a group of healthy persons and a group of non-healthy persons from each other with respect to sets of the assignments, the measurement regions, and the feature amounts.

Additionally, as illustrated in FIG. 6, in the brain activity feature amount extraction method of the present embodiment, index values serving as indexes indicating effectiveness or non-effectiveness for discriminating the group of healthy persons and the group of non-healthy persons from each other with respect to sets of the tasks, the measurement regions, and the feature amounts are calculated (refer to Step S4 of FIG. 8). Specifically, a plurality of the subjects P are classified into a group of cognitive function healthy persons (hereinafter referred to as NDC), and a group of mild cognitive function disabled persons (hereinafter referred to as MCI). Then, index values serving as indexes indicating whether or not NDC and MCI can be discriminated are calculated on several conditions that combinations of the assignments, the measurement regions, and the feature amounts are different. The calculation of the index values is performed using significant differences (p values) in Mann-Whitney U tests and Youden-Index serving as indexes of sensitivity and specificity. In addition, p values and Youden-Index are examples of an "index value" of the claims.

In addition, in the table of FIG. 6, p-value, Task, Channel, and Signal show the type of signals serving as indexes of the p values, the type of tasks, the measurement regions, and changes in the cerebral blood flow rate, respectively. In Task, Reikan, Keisan, Sumanu, and Kuukan respectively show a task in which the cold sensory stimulation is given to the subjects P, a task in which the calculation problem is given to the subjects P, a task in which the problem of guessing the similar letters is given to the subjects P, and, a task in which the problem of answering where to stand to see the landscape of the landscape photograph with a number is given to the subjects P. In Signal, Oxyhb, Deoxyhb, and Totalhb show the change in the amount of oxygenated hemoglobin, the change in the amount of deoxygenated hemoglobin, and the change of the total amount of hemoglobin, respectively. In addition, Oxyhb may relatively sensitively react even on the tasks (a dynamic range is high), while sensitively reacting even on factors, such as the body motion of the subjects P, other than the tasks. As a result, there is a case where noise is included in a measurement result. On the other hand, since Deoxyhb is insensitive to the body motion or the like of the subjects P (is accurate with respect to localization of a brain activity region), a measurement result with relatively little noise can be obtained by using Deoxyhb as an index of the change in the cerebral blood flow rate.

Additionally, in the table of FIG. 6, Feature_type, Feature_combi, and Trial show the type of the feature amounts, combinations of the feature amounts, and tasks for calculating the feature amounts, respectively. In Feature_type, Feature1, Feature2, Feature3, Feature4, Feature5, Feature11, and Feature21 show the feature amount 1, the feature amount 2, the feature amount 3, the feature amount 4, the feature amount 5, the feature amount 11, and the feature amount 21, respectively. Feature_combi represents combinations of trials of the tasks. For example, "Trial-3" in data described in the top row of FIG. 6 has a measurement result in a third trial when the task "Sumanu" is tried multiple times (for example, four times) as a feature amount. In this case, since only a measurement result of one trial is used as the feature amount, "Feature_combi" is set to "Single." Additionally, "Trial-2×4" in data described in a second row from above in FIG. 6 has a difference between respective measurement results in second and fourth trials when the task "Reikan" is tried multiple times (for example, four times) as a feature amount. In this case, since measurement results of two trials are used as a difference, "Feature_combi" is set to "Diff." Additionally, "Trial-3×4" in data described in the fourteenth row from above in FIG. 6 has a ratio of respective measurement results in third and fourth trials when the task "Reikan" is tried multiple times (for example, four times) as a feature amount. In this case, since a ratio of measurement results of two trials is used, "Feature_combi" is set to "Ratio."

Additionally, in the brain activity feature amount extraction method of the present embodiment, a plurality of data items in which the sets of the assignments, the measurement regions, and the feature amounts are associated with the calculated index values are acquired. Additionally, in the brain activity feature amount extraction method of the present embodiment, the plurality of data items associated with the index values are rearranged in order of higher effectiveness (refer to Step S6 of FIG. 8). Additionally, in the brain activity feature amount extraction method of the present embodiment, combinations of the plurality of acquired data items are displayed in order of higher effectiveness (refer to Step S7 of FIG. 8).

Specifically, in the brain activity feature amount extraction method of the present embodiment, the sets of the assignments, the measurement regions, and the feature amounts are associated with the calculated index values (refer to Step S5 of FIG. 8). Although 20 data items in which the sets of the assignments, the measurement regions, and the feature amounts are associated with the index values are illustrated in FIG. 6, the number of data items to be calculated in practice is not limited to this. Also, the data items in which the sets of the assignments, the measurement regions, and the feature amounts are associated with the index values are rearranged in order of the index values with higher effectiveness. In FIG. 6, the associated data items 1 to 20 are arranged in order of smaller p values. Then, the data items rearranged in order of the index values with higher effectiveness are displayed on a display unit (not illustrated) for allowing a person (doctor or the like) who performs the extraction of the brain activity feature amounts to check the data.

Figure 7:
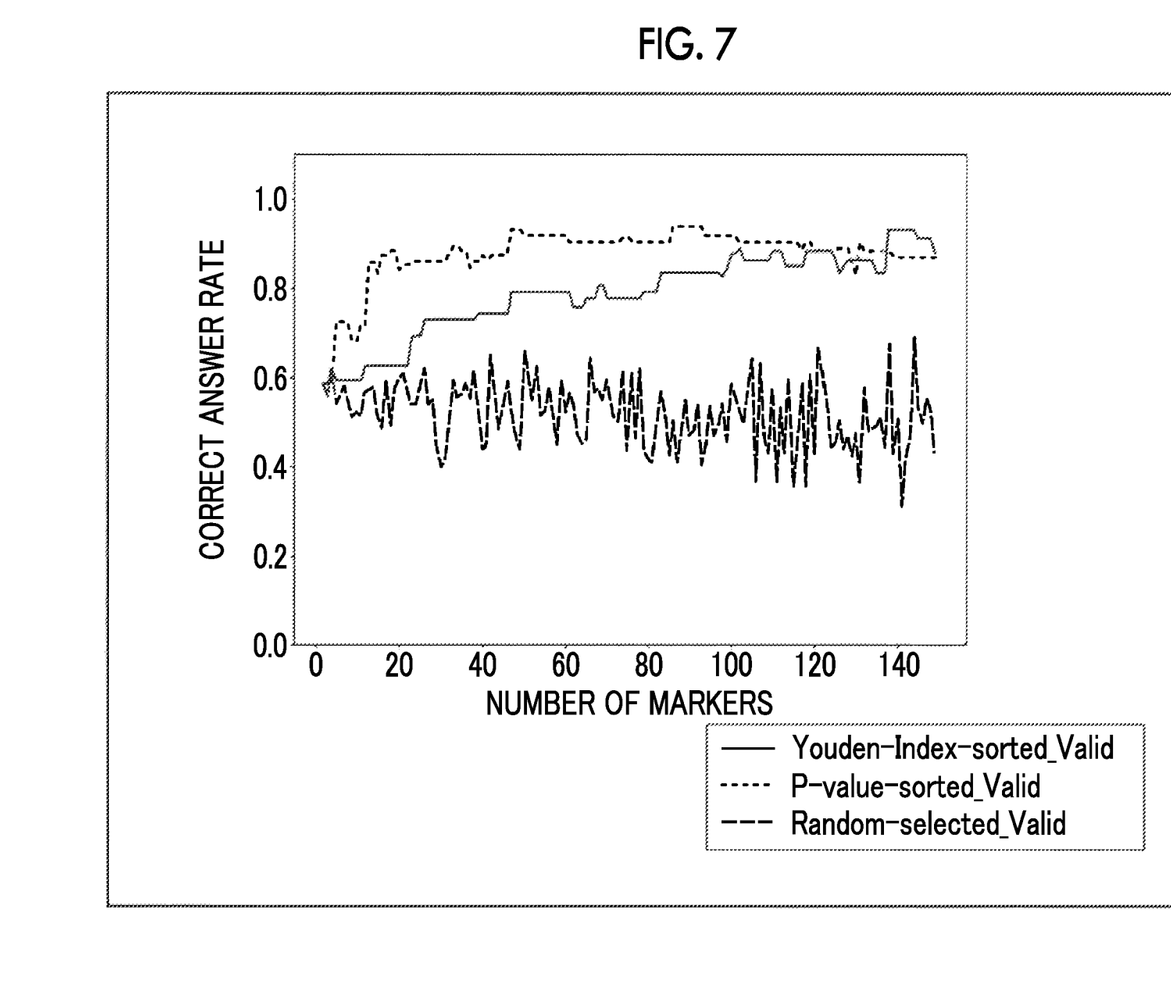
FIG. 7 is a view for illustrating trials for discriminating whether subjects are healthy persons or non-healthy persons and correct answer rates thereof.

Additionally, as illustrated in FIG. 7, in the brain activity feature amount extraction method of the present embodiment, the combination of the plurality of data items is acquired in order of higher effectiveness for discriminating whether the subjects are healthy persons or non-healthy persons, among the plurality of data items on the basis of the calculated index values. Then, a plurality of regression models with different numbers of the plurality of data items are created, and the number of the data items required to discriminate whether the subjects P are healthy persons or non-healthy persons is acquired on the basis of respective correct answer rates of the plurality of created regression models.

Specifically, in the brain activity feature amount extraction method of the present embodiment, the plurality of regression models for discriminating whether the subjects P are healthy persons or non-healthy persons are created (refer to Step S9 of FIG. 8) on the basis of the plurality of combinations of the plurality of acquired (displayed) data items. For example, as illustrated in FIG. 7, the regression models are created, respectively, while the number of the plurality of data items (markers) is increased. Then, respective correct answer rates when discriminating whether the subjects P are healthy persons or non-healthy persons are acquired on the basis of created regression models (refer to Step S10 of FIG. 8). Then, on the basis of the acquired respective correct answer rates, the combinations and the number of the data items required to discriminate whether the subjects P are healthy persons or non-healthy persons are acquired.

More specifically, as illustrated in FIG. 7, in the brain activity feature amount extraction method of the present embodiment, the number of combinations of the data items rearranged in order of the index values with higher effectiveness illustrated in FIG. 6 is changed, and logistic regression trials are performed and the correct answer rates for discriminating NDC and MCI from each other are acquired. In the logistic regression trials, regression models in which objective variables are binary values (NDC:0-MCI: 1) are built. Then, verification for discriminating the binary values is performed using the built regression models to acquire the correct answer rates. As the verification, for example, 10-division cross verification is performed. As a result, as illustrated in FIG. 7, the correct answer rates by the cross verification for discriminating the binary values are high as the number of the data items rearranged in order of smaller p values increases. In addition, correct answer rates of the cross verification in a case where the data items rearranged on the basis of the p values are used, correct answer rates of the cross verification in a case where the data items rearranged on the basis of Youden-Index are used, and, correct answer rates of the cross verification in a case where the randomly arranged data items are used are illustrated in FIG. 7. Then, the combinations and the number of the data items required to discriminate whether the subjects P are NDC or MCI are acquired on the basis of the acquired correct answer rates.

In addition, in the brain activity feature amount extraction method of the present embodiment, the number of the data items in which the correct answer rates is equal to or more than a predetermined threshold is acquired. For example, in an example illustrated in FIG. 7, the number of the data items required to discriminate whether the subjects P are healthy persons or non-healthy persons are equal to or more than 20. Specifically, in the example illustrated in FIG. 7, in a case where the data items rearranged on the basis of the p values are used, the correct answer rates of the cross verification reach substantially 90% in the number of the data items of 40 or more and 60 or less. Thus, the combinations of data items required to discriminate whether the subjects P are NDC or MCI are combinations of data items of top-rank 40 or more and 60 or less that are rearranged on the basis of the p values. In addition, the number of the data items required to discriminate whether the subjects P are healthy persons or non-healthy persons depends on measurement target groups.

(Flow for Acquiring Determination Criteria)

Next, a flow for acquiring the combination and the number (a sufficient number of determination criteria for discriminating whether a subject P is a healthy person or a non-healthy person) of the plurality of data items for discriminating whether the subject P is a healthy person or a non-healthy person will be described with reference to FIG. 8.

First, Step S1, a task for triggering brain activity is given to the subject P including the group of healthy persons and the group of non-healthy persons. In addition, in Step S1, a plurality of times of the tasks with different difficulty degrees in the same task are given.

Next, in Step S2, the change in the cerebral blood flow rate for each measurement region of the subject P when the task is given to the subject P is measured. In addition, in Step S2, the change in the amount of oxygenated hemoglobin, the change in the amount of deoxygenated hemoglobin, and the total amount of hemoglobin are measured as the indexes of the change in the cerebral blood flow rate.

Next, in Step S3, the feature amounts relating to the change in the cerebral blood flow rate are acquired. In addition, in Step S3, as the feature amounts relating to the change in the cerebral blood flow rate, the period in which the average value of the change in the cerebral blood flow rate is changed, and the plurality of kinds of the average values (feature amounts 1 to 5) of the changes in the cerebral blood flow rate acquired on the basis of the average value of the change in the cerebral blood flow rate in the predetermined period included in the task period and the average value of the change in the cerebral blood flow rate in the predetermined period included in the rest period, the area center of gravity (feature amount 11) of the region formed by the curved line showing the change in the cerebral blood flow rate in the task period, and the maximum value (feature amount 21) of the gradient in the curved line showing the change in the cerebral blood flow rate in the task period are required.

Next, in Step S4, the index values (the p values and Youden-Index) serving as the indexes indicating effectiveness or non-effectiveness for discriminating the group of healthy persons and the group of non-healthy persons from each other with respect to the sets of the tasks, the measurement regions, and the feature amounts are calculated.

Next, in Step S5, the sets of the tasks, the measurement regions, and the feature amounts are associated with the calculated index values (the p values and Youden-Index) calculated in Step S4.

Next, in Step S6, the data items in which the sets of the tasks, the measurement regions, and the feature amounts are associated with the calculated index values are rearranged in order of the index values (the p values and Youden-Index) with higher effectiveness.

Next, in Step S7, the combination of the plurality of data items rearranged in Step S6 is displayed on the display unit (not illustrated) for allowing a person (doctor or the like) who performs the extraction of the brain activity feature amounts to check the data.

Next, in Step S8, the plurality of combinations of the plurality of data items displayed in Step S7 are acquired by changing the number of data items.

Next, in Step S9, the plurality of regression models for discriminating whether the subject P is a healthy person or a non-healthy person are respectively created on the basis of the plurality of combinations of the plurality of data items acquired in Step S8.

Next, in Step S10, the respective correct answer rates when discriminating whether the subject P is a healthy person or a non-healthy person are acquired on the basis of the regression models created in Step S9.

Next, in Step S11, on the basis of the respective correct answer rates acquired in Step S10, the combinations and the number (a sufficient number of determination criteria for discriminating whether the subject P is a healthy person or a non-healthy person) of the data items required to discriminate whether the subject P is a healthy person or a non-healthy person are required.

(Effects of Embodiment)

The following effects can be obtained in the present embodiment.

In the present embodiment, as described above, the combination of the plurality of data items is acquired in order of higher effectiveness for discriminating whether the subject P is a healthy person or a non-healthy person, among the plurality of data items associated with the index values on the basis of the index value serving as the index indicating effectiveness or non-effectiveness for discriminating the group of healthy persons and the group of non-healthy persons from each other. Then, the combinations of the plurality of acquired data items are displayed in order of higher effectiveness. Accordingly, the plurality of data items associated with the index values are displayed in order of higher effectiveness for discriminating whether the subject P is a healthy person or a non-healthy person. Thus, the plurality of data items associated with the index values with high effectiveness can be easily ascertained. As a result, the occurrence of extraction omission of the feature amounts (determination criteria) useful for discriminating whether the subject P is a healthy person or a non-healthy person can be suppressed. Thus, a situation, in which whether the subject P is a healthy person or a non-healthy person cannot be appropriately discriminated due to the extraction omission of the useful determination criteria, can be suppressed.

Additionally, in the present embodiment, as described above, the plurality of models with different numbers of the data items can be created with respect to the displayed combination of the plurality of data items, and the number of the data items required to discriminate whether the subject P is a healthy person or a non-healthy person is acquired on the basis of the respective correct answer rates of the plurality of created models. Accordingly, the number of the data items required (in acquisition and display) to discriminate whether the subject P is a healthy person or a non-healthy person can be easily ascertained on the basis of the correct answer rates of the plurality of models with different numbers of the data items.

Additionally, in the present embodiment, as described above, the plurality of regression models with different numbers of the plurality of data items are created, and the number of the data items required to discriminate whether the subject P is a healthy person or a non-healthy person is acquired on the basis of the respective correct answer rates of the plurality of created regression models. Accordingly, the number of the data items required to discriminate whether the subject P is a healthy person or a non-healthy person can be easily acquired on the basis of the respective correct answer rates of the plurality of regression models.

Additionally, in the present embodiment, as described above, the number of the data items in which the correct answer rates are equal to or more than the predetermined threshold is acquired. Accordingly, the number of the data items required to discriminate whether the subject P is a healthy person or a non-healthy person can be easily determined on the basis of the predetermined threshold.

Additionally, in the present embodiment, as described above, the plurality of data items associated with the index values are rearranged in order of higher effectiveness. Accordingly, the combinations of the plurality of acquired data items can be easily displayed in order of higher effectiveness.

Additionally, in the present embodiment, as described above, the period in which the average value of the change in the cerebral blood flow rate is changed, and the plurality of kinds of the average values of the changes in the cerebral blood flow rate acquired on the basis of the average value of the change in the cerebral blood flow rate in the predetermined period included in the task period 31 and the average value of the change in the cerebral blood flow rate in the predetermined period included in the rest period 32 are acquired as the feature amounts relating to the change in the cerebral blood flow rate. Accordingly, the feature amounts relating to the change in the cerebral blood flow rate can be acquired from the plurality of kinds of the average values of the changes in the cerebral blood flow rate. Thus, the number of the plurality of data items for discriminating the group of healthy persons and the group of non-healthy persons from each other can be effectively increased. As a result, it is possible to acquire a more sufficient number of determination criteria for discriminating whether the subject P is a healthy person or a non-healthy person.

Additionally, in the present embodiment, as described above, the area center of gravity of the region formed by the curved line showing the change in the cerebral blood flow rate in the task period 31 and the maximum value of the gradient in the curved line showing the change in the cerebral blood flow rate are acquired as the feature amounts relating to the change in the cerebral blood flow rate. Accordingly, there is a case where area centers of gravity or maximum values of the gradient are different even if average values of changes in the cerebral blood flow rate in a certain period are the same. Thus, whether the subject P is a healthy person or a non-healthy person can be accurately discriminated by including at least one of the area center of gravity or the maximum value of the gradient included as a feature amount relating to the change in the cerebral blood flow rate.

Additionally, in the present embodiment, as described above, the plurality of tasks with different difficulty degrees in the same task are given. Additionally, the differences or ratios between the average values in the cerebral blood flow rate in task periods with mutually different difficulty degrees are acquired as the feature amounts. Accordingly, changes in the brain activity caused by tasks of difficulty degrees according to subjects P can be measured. Thus, even when there are individual differences in adaptation of the subjects P to the tasks, the degree of the cognitive function can be determined.

Additionally, in the present embodiment, as described above, the sensory stimulation, the calculation, the memory, the imagination, and the spatial cognition for the subject P are given to the subject P as the tasks. Accordingly, the plurality of kinds of tasks that trigger the brain activity can be given to the subject P. Thus, the number of the plurality of data items for discriminating the group of healthy persons and the group of non-healthy persons from each other can be effectively increased. As a result, it is possible to acquire a further sufficient number of determination criteria for discriminating whether the subject P is a healthy person or a non-healthy person.

Additionally, in the present embodiment, as described above, the change in the amount of oxygenated hemoglobin, the change in the amount of deoxygenated hemoglobin, and, the change in the total amount of hemoglobin that is a total amount of the amount of oxygenated hemoglobin and the amount of deoxygenated hemoglobin are measured as the indexes of the change in the cerebral blood flow rate. Accordingly, the change in the cerebral blood flow rate of the subject P can be acquired by the plurality of kinds of indexes. Thus, the number of the plurality of data items for discriminating the group of healthy persons and the group of non-healthy persons from each other can be effectively increased. As a result, it is possible to acquire a further sufficient number of determination criteria for discriminating whether the subject P is a healthy person or a non-healthy person.

Additionally, in the present embodiment, as described above, the changes in the cerebral blood flow rate for the respective measurement regions set as the ranges including F3, F4, P3, and P4 of the international 10-20 method are measured. Accordingly, changes in the cerebral blood flow rate in ranges (the frontal association cortex, the motor cortex, the interval cortex) generally used when brain waves are measured can be measured. Thus, the change in the cerebral blood flow rate with respect to the task can be appropriately measured.

Additionally, in the present embodiment, as described above, the change in the cerebral blood flow rate for each measurement region is measured by the near-infrared spectroscopy (NIRS). Accordingly, the change in the cerebral blood flow rate of the subject P can be measured using the NIRS apparatus. As a result, the NIRS apparatus is non-invasive, and does not need a large-scale facility as compared to magnetic resonances imaging (MRI) or the like. Thus, the change in the cerebral blood flow rate of the subject can be simply measured.

Modification Example

In addition, the embodiment disclosed this time is considered as illustrative in all points and not restrictive. The scope of the present invention is shown not by the description of the above-described embodiment but by the claims, and includes all changes (modification examples) in meanings and scope equivalent to those of the claims.

For example, in the above embodiment, an example in which the change in the amount of oxygenated hemoglobin, the change in the amount of deoxygenated hemoglobin, and the total amount of hemoglobin are measured has been shown. However, the present invention is not limited to this. In the present invention, only the change in the amount of oxygenated hemoglobin may be measured, or only the change in the amount of deoxygenated hemoglobin may be measured and only the change in the total amount of hemoglobin may be measured.

Additionally, in the above embodiment, an example in which the combinations and the number of the data items required to discriminate whether the subject P is a healthy person or a non-healthy person are acquired by the data items rearranged on the basis of the p values has been shown. However, the present invention is not limited to this. In the present invention, the combinations and the number of the data items required to discriminate whether the subject P is a healthy person or a non-healthy person are acquired by the data items rearranged on the basis of Youden-Index.

Additionally, in the above embodiment, an example in which Youden-Index is used as the indexes of the sensitivity and the specificity has been shown. However, the present invention is not limited to this. In the present invention, those other than Youden-Index may be used as the indexes of the sensitivity and the specificity. For example, AUC may be used.

Additionally, in the above embodiment, an example has been shown in which the calculation of the index values serving as the indexes indicating effectiveness or non-effectiveness for discriminating the group of healthy persons and the group of non-healthy persons from each other with respect to the sets of the tasks, the measurement regions, and the feature amounts is performed using the significant differences (p values) in the Mann-Whitney U tests and Youden-Index serving as the indexes of the sensitivity and the specificity. However, the present invention is not limited to this. In the present invention, the calculation of the index values serving as the indexes indicating effectiveness or non-effectiveness for discriminating the group of healthy persons and the group of non-healthy persons from each other with respect to the sets of the tasks, the measurement regions, and the feature amounts may be performed using other index values.

Additionally, in the above embodiment, an example in which the cold sensory stimulation is given to the subject P has been shown as a task for giving the sensory stimulation to the subject P. However, the present invention is not limited to this. In the present invention, as long as tasks capable of giving the sensory stimulation to sensory organs of the subject P are provided, the sensory stimulation for the subject P may be other than the cold sensory stimulation.

Additionally, in the above embodiment, the problem or the like in which 7 is consecutively subtracted from 100 in a case where the calculation problem is given to the subject P has been used. However, the present invention is not limited to this. In the present invention, any calculation problem of the four arithmetic operations may be used.

Additionally, in the above embodiment, an example in which, in a case where tasks given to the subject P are the memory and the imagination, the similar letters are written on the hand of the subject P and the problem in which the subject P guesses the letters is given has been shown. However, the present invention is not limited to this. In the present invention, in a case where tasks given to the subject P are the memory and the imagination, other problems may be given.

Additionally, in the above embodiment, an example in which the problem of answering where to stand to see the landscape of the landscape photograph with a number is given to the subject P in a case where a task given to the subject P is the spatial cognition has been shown. However, the present invention is not limited to this. In the present invention, in a case where a task given to the subject P is the spatial cognition, other problems may be given.

Additionally, in the above embodiment, an example in which the sensory stimulation, the calculation, the memory, the imagination, and the spatial cognition for the subject P are given to the subject P as the tasks has been described. However, the present invention is not limited to this. In the present invention, tasks other than the sensory stimulation, the calculation, the memory, the imagination, and the spatial cognition for the subject P may be given to the subject P.

Additionally, in the above embodiment, an example in which the plurality of tasks with different difficulty degrees in the same task are given has been shown. However, the present invention is not limited to this. In the present invention, a plurality of tasks having the same difficulty degree in the same task may be given.

Additionally, in the above embodiment, an example in which the seven feature amounts of the feature amount 1, the feature amount 2, the feature amount 3, the feature amount 4, the feature amount 5, the feature amount 11, and the feature amount 21 are acquired as the feature amounts relating to the change in the cerebral blood flow rate has been shown. However, the present invention is not limited to this. In the present invention, as the feature amounts relating to the change in the cerebral blood flow rate, at least any one may be acquired from the feature amount 1, the feature amount 2, the feature amount 3, the feature amount 4, the feature amount 5, the feature amount 11, and the feature amount 21, or any two to six may be acquired therefrom. Additionally, feature amounts other than the feature amount 1, the feature amount 2, the feature amount 3, the feature amount 4, the feature amount 5, the feature amount 11, and the feature amount 21 may be acquired.

Additionally, in the above embodiment, an example in which the correct answer rates are acquired by performing the 10-division cross verification when it is discriminated whether the subject P is a healthy person or a non-healthy person has been shown. However, the present invention is not limited to this. In the present invention, when it is discriminated whether the subject P is a healthy person or a non-healthy person, the correct answer rates may be acquired by performing methods other than the 10-division cross verification.

Additionally, in the above embodiment, an example in which the logistic regression trials are performed when the number of the data items required to discriminate whether the subject P is a healthy person or a non-healthy person is acquired has been shown. However, the present invention is not limited to this. In the present invention, when the number of the data items required to discriminate whether the subject P is a healthy person or a non-healthy person is acquired, regression trials or machine learning other than the logistic regression trials may be performed.

Additionally, in the above embodiment, an example in which the number of the data items required to discriminate whether the subject P is a healthy person or a non-healthy person is acquired has been described. However, the present invention is not limited to this. In the present invention, the number of the data items required to discriminate whether the subject P is a healthy person or a non-healthy person may be acquired. In this case, in the flow of FIG. 8, steps subsequent to the step (Step S8) of acquiring the plurality of combinations of the plurality of data items displayed on the display unit by changing the number of data items may be omitted.

What is claimed is:

1. A brain activity feature amount extraction method, comprising:
  giving, displayed on a display device, an assignment for triggering brain activity to a subject including a group of healthy persons and a group of non-healthy persons;
  measuring a change in a cerebral blood flow rate for each measurement region of the subject when the assignment is given to the subject;
  acquiring a feature amount relating to the change in the cerebral blood flow rate;
  calculating an index value serving as an index indicating effectiveness or non-effectiveness for discriminating the group of healthy persons and the group of non-healthy persons from each other with respect to each combination of the assignment, the measurement region, and the feature amount that the each combination includes the assignment, the measurement region, and the feature amount;

acquiring a plurality of data items in which the set of the assignment, the measurement region, and the feature amount is associated with the calculated index value;

acquiring a combination of the plurality of data items in order of higher effectiveness for discriminating whether the subject is a healthy person or a non-healthy person, among the plurality of data items on a basis of the calculated index value; and displaying, on the display device to the subject, the combination of the plurality of acquired data items in order of higher effectiveness.

2. The brain activity feature amount extraction method according to claim 1, further comprising:

creating a plurality of models with different numbers of the plurality of data items with respect to the displayed combination of the plurality of data items, and acquiring a number of the plurality of data items required to discriminate whether the subject is the healthy person or the non-healthy person on a basis of a correct answer rate of each of the plurality of created models.

3. The brain activity feature amount extraction method according to claim 2, wherein the acquiring the number of the plurality of data items further includes creating a plurality of regression models with different numbers of the plurality of data items, and acquiring the number of the plurality of data items required to discriminate whether the subject is the healthy person or the non-healthy person on the basis of the correct answer rate of each of the plurality of created regression models.

4. The brain activity feature amount extraction method according to claim 2, wherein the acquiring the number of the plurality of data items includes acquiring the number of the plurality of data items in which the correct answer rate is equal to or more than a predetermined threshold.

5. The brain activity feature amount extraction method according to claim 1, further comprising:

rearranging the plurality of data items associated with the index value in order of higher effectiveness.

6. The brain activity feature amount extraction method according to claim 1, wherein the acquiring the feature amount relating to the change in the cerebral blood flow rate includes changing a period in which an average value of the change in the cerebral blood flow rate is acquired, and acquiring at least one of a plurality of kinds of average values of changes in the cerebral blood flow rate acquired on a basis of an average value of the change in the cerebral blood flow rate in a predetermined period included in a period in which the assignment is performed and an average value of the change in the cerebral blood flow rate in a predetermined period included in a period in which the assignment is not performed, as the feature amount relating to the change in the cerebral blood flow rate.

7. The brain activity feature amount extraction method according to claim 1, wherein the acquiring the feature amount relating to the change in the cerebral blood flow rate includes acquiring at least one of an area center of gravity of a region formed by a curved line showing the change in the cerebral blood flow rate in a period where the assignment is performed or a maximum value of a gradient in a curved line showing the change in the cerebral blood flow rate as the feature amount relating to the change in the cerebral blood flow rate.

8. The brain activity feature amount extraction method according to claim 1, wherein the giving an assignment includes giving a plurality of the assignments with different difficulty degrees in a same assignment, and wherein the acquiring the feature amount relating to the change in the cerebral blood flow rate includes acquiring a difference or a ratio of average values of the cerebral blood flow rates between periods in which the plurality of assignments with different difficulty degrees are performed as the feature amount.

9. The brain activity feature amount extraction method according to claim 1, wherein the giving the assignment includes giving at least one of sensory stimulation, calculation, memory, imagination, and spatial cognition for the subject as the assignment to the subject.

10. The brain activity feature amount extraction method according to claim 1, wherein the measuring the change in the cerebral blood flow rate includes, as the index of the change in the cerebral blood flow rate, measuring at least one of a change in an amount of oxygenated hemoglobin, a change in an amount of deoxygenated hemoglobin, and, a change in a total amount of hemoglobin that is a total amount of the amount of oxygenated hemoglobin and the amount of deoxygenated hemoglobin.

11. The brain activity feature amount extraction method according to claim 1, wherein the measuring the change in the cerebral blood flow rate of each measurement region includes measuring a change in the cerebral blood flow rate for each measurement region set to a range including at least one of F3, F4, P3, and P4 of an international 10-20 method.

12. The brain activity feature amount extraction method according to claim 1, wherein the measuring the change in the cerebral blood flow rate for each measurement region includes measuring the change in the cerebral blood flow rate for each measurement region by near-infrared spectroscopy.

* * * * *